United States Patent [19]

Yokoyama et al.

[11] 4,035,399

[45] July 12, 1977

[54] PROCESS FOR THE PREPARATION OF 1,4-NAPHTHOQUINONE

[75] Inventors: Yoshio Yokoyama, Tokyo; Junzo Yoshikawa; Harutoshi Ota, both of Ichikawa, all of Japan

[73] Assignee: Nihon Joryu Kogyo Co., Ltd., Ichikawa, Japan

[21] Appl. No.: 681,920

[22] Filed: Apr. 30, 1976

Related U.S. Application Data

[63] Continuation-in-part of Ser. No. 550,043, Feb. 14, 1975, abandoned.

[30] Foreign Application Priority Data

Feb. 18, 1974 Japan .............................. 49-18523

[51] Int. Cl.$^2$ ......................................... C07C 49/66
[52] U.S. Cl. ........................... 260/396 R; 260/346.4
[58] Field of Search ..................... 260/396 R, 346.4

[56] References Cited

U.S. PATENT DOCUMENTS

| | | | |
|---|---|---|---|
| 2,765,323 | 10/1956 | Dixon et al. | 260/396 R |
| 2,989,544 | 6/1961 | Saunders et al. | 260/396 R |
| 3,095,430 | 6/1963 | Wettstein | 260/396 R |
| 3,232,955 | 2/1966 | Nonnenmacher | 260/396 R |
| 3,379,741 | 4/1968 | Ischampen | 260/396 N |
| 3,402,187 | 9/1968 | Kaiser et al. | 260/396 R |
| 3,897,464 | 7/1975 | Dohm et al. | 260/396 R |

*Primary Examiner*—Vivian Garner
*Attorney, Agent, or Firm*—Armstrong, Nikaido & Marmelstein

[57] ABSTRACT

In the process for the preparation of 1,4-naphthoquinone by vapor phase oxidation of naphthalene with a molecular oxygen containing gas using a solid catalyst consisting essentially of an inert carrier supporting thereon a catalyst composition comprising as essential active components vanadium pentoxide, an alkali metal sulfate and an alkali metal pyrosulfate, the improvement which comprises supplying to the raw material feed sulfur or a sulfur compound capable of yielding sulfur trioxide in a system as to maintain the equilibrium between the alkali metal sulfate and the alkali metal pyrosulfate in the catalyst composition and keep the proportion of the active components constant.

13 Claims, No Drawings

PROCESS FOR THE PREPARATION OF 1,4-NAPHTHOQUINONE

CROSS REFERENCE TO RELATED APPLICATIONS

This application is a continuation-in-part of our copending application Ser. No. 550,043 filed Feb. 14, 1975, now abandoned.

This invention relates to a process for the preparation of 1,4-naphthoquinone by catalytic vapor phase oxidation of naphthalene. More particularly, it relates to an improvement in the process for the preparation of 1,4-naphthoquinone by catalytic vapor phase oxidation of naphthalene with a molecular oxygen containing gas in the presence of a vanadium pentoxide-alkali metal sulfate-alkali metal pyrosulfate catalyst, which comprises maintaining the concentration of sulfuric anhydride in a system within a definite range as to maintain the activity and selectivity of the catalyst at a high level for a long period of time.

It has hitherto been known in the art to produce 1,4-naphthoquinone by catalytic vapor phase oxidation of naphthalene by means of a molecular oxygen containing gas and it also is well knwon to use catalysts consisting of a catalyst composition comprising vanadium pentoxide, an alkali metal sulfate and an alkali metal pyrosulfate and, optionally, other metal oxides and supported on a carrier, as disclosed in Japanese Patent Specification published for public inspection Nos. 5533/1967 and 15063/1968 and Japanese Patent Specification laid open No. 19489/1973. In the prior processes, however, it is difficult to prepare 1,4-naphthoquinone as a sole product and there is yielded inevitably phthalic anhydride as a by-product. In order to obtain 1,4-naphthoquinone in a high yield, accordingly, it is essential to minimize the yield of phthalic anhydride or the selectivity thereto while keeping the total conversion as high as possible. However, in practice and in theory, the maximum yield of 1,4-naphthoquinone is obtained when the ratio of the yield of 1,4-naphthoquinone to that of phthalic anhydride is 50:50. Accordingly, it would be the present target of the maximum yield of 1,4-naphthoquinone in commercial production to obtain 50 parts by weight of 1,4-naphthoquinone per 100 parts by weight of the starting naphthalene. In some cases the above object may be attained by usng a known catalyst under a known condition in the initial period of reaction run, though the yield of 1,4-naphthoquinone decreases remarkably with gradual increase of the yield of phthalic anhydride with the elapse of reaction time. This is, of course, attributable to the changes with the elapse of time in catalytic activity and selectivity of the catalyst, and such a catalyst is impractical for commercial production of 1,4-naphthoquinone from naphthalene because of its very short life time.

Accordingly, an object of the present invention is to provide an improved process for the production of 1,4-naphthoquinone by catalytic vapor phase oxidation of naphthalene.

Another object of the present invention is to provide an improved process for the production of 1,4-naphthoquinone by catalytic vapor phase oxidation of naphthalene by means of a molecular oxygen containing gas in the presence of a vanadium pentoxide-alkali metal sulfate-alkali metal pyrosulfate catalyst, in which the activity and selectivity of the catalyst are kept high for a long period of time.

The above objects are attained by an improvement in a process for the preparation of 1,4-naphthoquinone by catalytically oxidizing in vapor phase naphthalene by means of a molecular oxygen containing gas in the presence of a solid catalyst comprising an inert carrier supporting thereon a catalytic substance comprising a mixture of vanadium pentoxide, an alkali metal sulfate and an alkali metal pyrosulfate and, optionally, other metal compounds, which improvement comprises supplying sulfur or a sulfur compound to a feed so as to maintain in the system a sulfur trioxide concentration requisite for maintaining the equilibrium between the alkali metal sulfate and the alkali metal pyrosulfate in the catalytic substance and keeping the proportion thereof constant.

It has already been known that the activity and the selectivity of a catalyst comprising a catalytic substance consisting essentially of vanadium pentoxide, an alkali metal sulfate and an alkali metal pyrosulfate and, optionally, other metal oxides, supported on an inert carrier, varies depending on the ratio of the sulfate to the pyrosulfate. Namely, the activity decreases as the proportion of a sulfate increases and, correspondingly, that of a pyrosulfate decreases and, in contrast, it increases as the proportion of the sulfate decreases and, correspondingly, that of the pyrosulfate increases and, as the result, the yield of phthalic anhydride is decreased while that of 1,4-naphthoquinone is increased. Accordingly, it is necessary for obtaining 1,4-naphthoquinone steadily in a high yield over a long period of time to maintain the optimum ratio of the alkali metal sulfate to the alkali metal pyrosulfate in the catalytically active substance constant without any change throughout the reaction run.

With respect to the aforesaid catalyst, as the result of investigation, it has been found that, for instance in case of potassium sulfate and potassium pyrosulfate, there is established the following equilibrium therebetween:

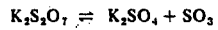

$$K_2S_2O_7 \rightleftharpoons K_2SO_4 + SO_3$$

The reaction proceeds rightward, i.e., $K_2S_2O_7$ decomposes, as the temperature rises and, on the other hand, it proceeds leftward, i.e., $K_2S_2O_7$ is formed, as the temperature lowers. At the reaction temperature, $K_2S_2O_7$ and $K_2SO_4$ are in a molten state on the surface of the carrier and $SO_3$ is in a gaseous state.

Naphthalene as starting material usually contains a sulfur compound in the total amount, calculated as elementary sulfur, of 0 to 0.6% by weight though the sulfur content varies depending on its source, e.g., coal tar or petroleum, or its grade, e.g., purified naphthalene or industrial naphthalene, and the sulfur compound is oxidized during the reaction to form $SO_3$. When various naphthalenes different in sulfur content are catalytically oxidized in vapor phase with a molecular oxygen containing gas by the aid of a catalyst consisting of an inert carrier supporting thereon $V_2O_5$, $K_2SO_4$ and $K_2S_2O_7$ as catalytically active components, in accordance with the correlation between the $SO_3$ concentration in the reaction system owing to $SO_3$ yielded by oxidative decomposition of sulfur compounds contained in naphthalene and the temperature, in case where the total concentration of $SO_3$ in the system, owing to $SO_3$ formed at a temperature at which the following reaction takes plate $$K_2S_2O_7 \leftarrow K_2SO_4 + SO_3 \quad (1),$$

exceeds the concentration requisite for maintaining the following equilibrium $$K_2S_2O_7 \rightleftharpoons K_2SO_4 + SO_3 \quad (2),$$

the proportion of $K_2S_2O_7$ in the active components increases while that of $K_2SO_4$ decreases to make the catalyst activated type and the yield of phthalic anhydride increases. At a temperature at which there takes place the following reaction $$K_2S_2O_7 \rightarrow K_2SO_4 + SO_3 \quad (3)$$

$SO_3$ formed by decomposition of the sulfur compounds escapes together with an oxidation product gas effluent and the quantity of the escaping $SO_3$ is larger than that of the $SO_3$ yielding from the sulfur compounds to lower the total $SO_3$ concentration in the system below a concentration requisite for maintaining the equilibrium indicated by the above equation (2), the proportion of $K_2S_2O_7$ in the active components decreases while that of $K_2SO_4$ increases to make the catalyst inactivated type.

We have noticed the phenomenon of the above equation (3) and discovered that 1,4-naphthoquinone is produced steadily in a high yield for a long period of time by previously adding $SO_3$ in an amount corresponding to the deficiency for maintaining the equilibrium of the equation (2) under the condition under which there occurs the phenomenon as indicated by the equation (3) to the feed gas as to maintain the equilibrium of the equation (2) and thereby to prevent deterioration in catalytic activity and selectivity to 1,4-naphthoquinone of the catalyst.

The previous addition of sulfur trioxide to the feed gas in accordance with the present invention may be attained by introducing directly sulfur trioxide into the feed gas or, alternately, by adding to the feed gas or raw material naphthalene a sulfur compound capable of forming sulfur troixide, reduced to the weight of elemental sulfur through catalytic oxidation in the system. The sulfur compound capable of forming sulfur troixide in the system includes, e.g., sulfur dioxide, hydrogen sulfide and like inorganic sulfur compounds; and mercaptans, such as methyl mercaptan, ethyl mercaptan, n-propyl mercaptan, isopropyl mercaptan, n-butyl mercaptan, 2-methylpropyl mercaptan, 3-methylpropyl mercaptan, 1,1-dimethylethyl mercaptan, cyclohexy mercaptan, benzyl mercaptan and 1-methylbenzyl mercaptan; tiophenes, such as thiophene itself, 2-methylthiophene, 3-methylthiophene, dimethylthiophene, benzothiophene and tetra-hydrothiophene; thioethers such as methyl sulfide, ethyl sulfide, butyl sulfide and benzyl sulfide; thiocyanates, such as methyl thiocyanate and ethyl thiocyanate, and like organic compounds.

The concentration of sulfur trioxide to be allowed to exist in the reaction system varies depending on the reaction temperature and may be, including sulfur trioxide derived from sulfur compounds contained inherently in starting naphthalene, 0.8 to 1.8 and preferably 1.0 to 1.7% by weight based on the weight of naphthalene. The reaction temperature may be 420° to 480° C and preferably 430° to 470° C. The equilibrium of the above equation (2) is maintained unchanged and the activity and selectivity to 1,4-naphthoquinone of the catalyst can be maintained high when the reaction temperature is 430° to 470° C and the $SO_3$ concentration is 1.0 to 1.7% by weight based on the weight of naphthalene.

As the molecular oxygen containing gas there may usually be used air. The concentration of naphthalene may usually be of 25 to 35 litre-air/g-naphthalene and the hourly space velocity may usually be 500 to 3,000 $hr^{-1}$, preferably of 1,000 to 2,000 $hr^{-1}$.

The catalyst used in the process of the present invention may be any of those solid catalysts prepared by supporting a catalytically active substance comprising vanadium pentoxide, an alkali metal sulfate and an alkali metal pyrosulfate and, optionally, a sulfate or oxide of another metal on an inert carrier, such as disclosed in British Pat. specification No. 1,055,124, Japanese Pat. Specification published for public inspection No. 15063/1968 and Japanese Pat. Specification laid open Nos. 34353/1972 and 19489/1973. The oxide of another metal includes those of tungsten, titanium, zirconium, tantalum, cesium, molybdenum, chromium, niobium, nickel, aluminum, iron and silver, though preferred are those of tungsten, titanium, zirconium and tantalum. The sulfate of another metal includes iron sulfate and the like.

The inert carrier includes diatomaceous earth, silica, alumina, silicon carbide, white carbon and the like. Among such inert carriers preferably used are those having such particle size distributions that particles of sizes of 1 to 75 microns amount to 10 to 80% by weight of the whole particles. The inert carrier is blended with the aforesaid catalytically active substance and then molded into pellets, spheres or like granules of an average particles size of 3 to 8, preferably 4 to 6 mm.

In the following Examples, all percentages are by weight unless otherwise designated.

EXAMPLE 1

An iron reaction tube of an inner diameter of 27 mm $\phi$ was packed with 800 ml of a pelletized catalyst of a particle size of 5 mm (diameter × 5 mm (length) containing 18.1% of vanadium pentoxide $V_2O_5$, 30.9% of potassium sulfate $K_2SO_4$, 27.8% of potassium pyrosulfate $K_2S_2O_7$ and 23.2% of silica $SiO_2$ and the reaction was carried out using an industrial grade naphthalene (purity 96%, Sulfur content 0.6%) and air under the conditions: Salt bath temperature 450° C, space hourly velocity 1,400 $hr^{-1}$ and naphthalene concentration 30 litre-air/g-naphthalene, with adding sulfur dioxide to the gaseous feed, to obtain the results as summarized in the following Table 1.

Table 1

| | $SO_2$ unadded | | | 0.8 wt. % $SO_2$ added* | | |
|---|---|---|---|---|---|---|
| Reaction time lapsed (hr) | Yield of 1,4-naphthoquinone (mol %) | Yield of phthalic anhydride (mol %) | Unreacted naphthalene (mol %) | Yield of 1,4-naphthoquinone (mol %) | Yield of phthalic anhydride (mol %) | Unreacted naphthalene (mol %) |
| 20 | 22.2 | 14.4 | 55.8 | 39.9 | 38.6 | 14.3 |
| 50 | 28.5 | 17.2 | 47.5 | 40.3 | 37.2 | 14.5 |
| 100 | 34.5 | 21.2 | 35.7 | 40.5 | 37.9 | 13.3 |
| 150 | 36.7 | 22.9 | 31.4 | 40.4 | 35.3 | 15.5 |

Table 1-continued

| Reaction time lapsed (hr) | SO₂ unadded | | | 0.8 wt. % SO₂ added* | | |
|---|---|---|---|---|---|---|
| | Yield of 1,4-naphthoquinone (mol %) | Yield of phthalic anhydride (mol %) | Unreacted naphthalene (mol %) | Yield of 1,4-naphthoquinone (mol %) | Yield of phthalic anhydride (mol %) | Unreacted naphthalene (mol %) |
| 200 | 36.6 | 24.6 | 30.3 | 40.6 | 36.2 | 14.2 |

*The amount of SO₂ added is the percentage of the weight of SO₂ reduced to elementary sulfur to that of starting anphthalene fed.

EXAMPLE 2

The reaction run as in Example 1 was repeated with adding varying amounts of sulfur dioxide to the gaseous feed and after 200 hours from the start of reaction the yields of 1,4-naphthoquinone and of phthalic anhydride were determined to obtain the results as summarized in the following Table 2.

Table 2

| Amount of SO₂ added (wt. %)* | Yield of 1,4-naphthoquinone (mol %) | Yield of phthalic anhydride (mol %) | Unreacted naphthalene |
|---|---|---|---|
| 0.0 | 35.4 | 23.7 | 32.3 |
| 0.2 | 37.9 | 28.3 | 25.3 |
| 0.4 | 39.7 | 32.6 | 17.7 |
| 0.8 | 41.1 | 37.3 | 12.9 |
| 1.2 | 37.4 | 48.3 | 5.8 |

*The amount of SO₂ added is the percentage of the weight of SO₂ reduced to elementary sulfur to that of starting naphthalene fed.

EXAMPLE 3

The same reaction run as in Example 1 was continued for a long period of time for determination of the life of the catalyst to obtain the results as summarized in the following Table 3.

EXAMPLE 4

The same procedure as in Example 1 was repeated except that the salt bath temperature was as indicated in the following Table 4 to obtain the results as summarized in the Table 4. The amount of sulfur dioxide was the percentage of the weight reduced to elementary sulfur to that of the naphthalene fed, and the yields were determined 500 hours after the start of reaction.

Table 4

| Salt bath temp. (° C) | SO₂ amount added* | Yield of 1,4-naphthoquinone (mol %) | Yield of phthalic anhydride (mol %) | Unreacted naphthalene (mol %) |
|---|---|---|---|---|
| 430 | 0 | 35.3 | 21.2 | 37.7 |
| | 0.3 | 36.7 | 39.5 | 18.6 |
| 440 | 0 | 35.0 | 25.4 | 33.9 |
| | 0.5 | 39.7 | 38.3 | 15.4 |
| 450 | 0 | 36.6 | 24.6 | 30.3 |
| | 0.8 | 40.6 | 36.2 | 14.2 |
| 470 | 0 | 25.8 | 27.2 | 36.5 |
| | 1.0 | 38.9 | 35.3 | 15.3 |

*The amount of SO₂ added is the percentage of the weight of SO₂ reduced to elementary sulfur to that of starting naphthalene fed.

EXAMPLE 5

The same reaction run as in Example 1 was repeated using a pelletized catalyst of a particle size of 5 mm φ × 5 mm consisting of 17.1% of vanadium pentoxide, 26.3% of potassium sulfate, 29.2% of potassium pyrosulfate and 22.1% of silica to obtain the results as summarized in the following Table 5.

Table 3

| Reaction time lapsed (hr) | SO₂ unadded | | | 0.8 wt.% SO₂ added* | | |
|---|---|---|---|---|---|---|
| | Yield of 1,4-naphthoquinone (mol %) | Yield of phthalic anhydride (mol %) | Unreacted naphthalene (mol %) | Yield of 1,4-naphthoquinone (mol %) | Yield of phthalic anhydride (mol %) | Unreacted naphthalene (mol %) |
| 500 | 35.9 | 31.0 | 20.3 | 40.5 | 35.7 | 14.4 |
| 1000 | 39.6 | 42.2 | 8.4 | 40.8 | 35.3 | 14.6 |
| 2000 | 37.2 | 45.1 | 5.0 | 41.1 | 37.4 | 13.0 |
| 5000 | —** | —** | —** | 41.2 | 36.7 | 14.1 |

*The amount of SO₂ added is the percentage of the weight of SO₂ reduced to elementary sulfur to that of starting naphthalene fed.
**Oxidation reaction cannot be carried out, because life of the catalyst is too short.

Table 5

| Reaction time lapsed (hr) | SO₂ unadded | | | 0.8 wt. % SO₂ added* | | |
|---|---|---|---|---|---|---|
| | Yield of 1,4-naphthoquinone (mol %) | Yield of phthalic anhydride (mol %) | Unreacted naphthalene (mol %) | Yield of 1,4-naphthoquinone (mol %) | Yield of phthalic anhydride (mol %) | Unreacted naphthalene (mol %) |
| 20 | 24.3 | 19.2 | 50.4 | 39.2 | 35.5 | 12.4 |
| 50 | 32.1 | 27.8 | 31.5 | 38.9 | 38.3 | 12.0 |
| 100 | 33.2 | 29.9 | 27.5 | 40.1 | 39.2 | 9.6 |
| 150 | 37.7 | 29.6 | 24.9 | 39.8 | 38.7 | 10.1 |
| 200 | 36.7 | 28.6 | 25.3 | 40.3 | 39.6 | 9.5 |

*The amount of SO₂ added is the percentage of the weight of SO₂ reduced to elementary sulfur to that of starting naphthalene fed.

EXAMPLES 6 to 9

For exploration of influences of various sulfur compounds, a similar reaction run as in Example 1 was repeated with adding sulfur trioxide, benzothiophene, methyl mercaptan or hydrogen sulfide in an amount corresponding to 0.8% as elementary sulfur based on the weight of the starting naphthalene fed, to obtain the results as summarized in the following Table 6. The yields shown in the Table 6 were determined 200 hours after the start of reaction run. Benzothiophene was added to starting naphthalene and sulfur trioxide, methyl mercaptan and hydrogen sulfide were introduced into the gaseous feed.

Table 6

| Example No. | Sulfur compound added | Yield of 1,4-naphthoquinone (mol %) | Yield of phthalic anhydride (mol %) | Unreacted naphthalene (mol %) |
|---|---|---|---|---|
| 6 | Sulfur trioxide | 41.4 | 38.8 | 13.6 |
| 7 | Benzothiophene | 38.9 | 37.2 | 14.2 |
| 8 | Methyl mercaptan | 37.5 | 36.2 | 15.1 |
| 9 | Hydrogen sulfide | 38.0 | 36.8 | 14.9 |

What is claimed is:

1. In a process for preparing 1,4-naphthoquinone by vapor phase oxidation of naphthalene wherein naphthalene is oxidized in the vapor phase at a temperature of 420° C to 480° C by means of a molecular oxygen containing gas in the presence of a solid catalyst consisting essentially of an inert carrier supporting thereon a catalytic substance mixture consisting essentially of vanadium pentoxide, an alkali metal sulfate, an alkali metal pyrosulfate and optionally, an oxide of a metal selected from the group consisting of tungsten, titanium, zirconium, tantalum, cesium, molybdenum, chromium, niobium, nickel, aluminum, iron and silver or iron sulfate, the improvement comprising supplying sulfur or a sulfur compound capable of yielding sulfur trioxide into the raw material feed so as to maintain the equilibrium between the alkali metal sulfate and the alkali metal pyrosulfate and keep the proportion thereof constant and maintaining the concentration of sulfur trioxide, reduced to the weight of elemental sulfur, in the reaction system at 0.8 to 1.8% by weight based on the weight of naphthalene.

2. A process of claim 1 in which the concentration of naphthalene is 25 to 35 liter-air/g-naphthalene.

3. A process of claim 1 in which the hourly space velocity is 500 to 3,000 hr⁻¹.

4. A process of claim 1 in which the sulfur compound is a member selected from the group consisting of sulfur trioxide, sulfur dioxide, hydrogen sulfide, mercaptans, thiophenes, thioethers and organic thiocyanates.

5. A process of claim 1 in which the sulfur compound is a member of the group consisting of sulfur trioxide, sulfur dioxide, hydrogen sulfide and mercaptans.

6. A process of claim 1 wherein the catalytic substance mixture includes an oxide of a metal selected from the group consisting of tungsten, titanium, zirconium, tantalum, cesium, molybdenum, chromium, niobium, nickel, aluminum, iron and silver.

7. A process of claim 1 wherein the catalytic substance mixture includes iron sulfate.

8. In a process for preparing 1,4-naphthoquinone by vapor phase oxidation of naphthalene wherein naphthalene is oxidized in the vapor phase at a temperature of 420° C 480° C at a naphthalene concentration of 25 to 35 litre-air/g-naphthalene and at a hourly space velocity of 500 to 3,000 hr⁻¹ in the presence of a solid catalyst consisting essentially of an inert carrier supporting thereon a catalytic substance mixture consisting essentially of vanadium pentoxide, and alkali metal sulfate, an alkali metal pyrosulfate and optionally, an oxide of a metal selected from the group consisting of tungsten, titanium, zirconium, tantalum, cesium, molybdenum, chromium, niobium, nickel, aluminum, iron and silver or iron sulfate, the improvement comprising supplying together with the raw material feed sulfur or a sulfur compound selected from the group consisting of sulfur, sulfur trioxide sulfur dioxide, hydrogen sulfide, mercaptans, thiophenes, thioethers and organic thiocyanates so as to maintain the equilibrium between the alkali metal sulfate and the alkali metal pyrosulfate in the said catalytic substance mixture and keep the proportion thereof constant, and maintaining the sulfur trioxide concentration, reduced to the weight of elemental sulfur, at 0.8 to 1.8% by weight based on the weight of naphthalene.

9. A process of claim 8 wherein the catalytic substance mixture includes an oxide of a metal selected from the group consisting of tungsten, titanium, zirconium, tantalum, cesium, molybdenum, chromium, niobium, nickel, aluminum, iron and silver.

10. A process of claim 8 wherein the catalytic substance mixture includes iron sulfate.

11. In a process for preparing 1,4-naphthoquinone by vapor phase oxidation of naphthalene wherein naphthalene is oxidized in the vapor phase at a temperature of 430° to 470° C at a naphthalene concentration of 25 to 35 litre-air/g-naphthalene and at an hourly space velocity of 1,000 to 2,000 hr$^{-1}$ in the presence of a solid catalyst consisting essentially of an inert carrier supporting thereon a catalytic substance mixture consisting essentially of vanadium pentoxide, an alkali metal sulfate, an alkali metal pyrosulfate and optionally, an oxide of a metal selected from the group consisting of tungsten, titanium, zirconium, tantalum, cesium, molybdenum, chromium, niobium, nickel, aluminum, iron and silver or iron sulfate, the improvement comprising supplying together with the raw material feed sulfur or a sulfur compound selected from the group consisting of sulfur, sulfur trioxide, sulfur dioxide, hydrogen sulfide and mercaptans so as to maintain the equilibrium between the alkali metal sulfate and the alkali metal pyrosulfate in the said catalytic substance mixture and keep the proportion thereof constant, and maintaining the sulfur trioxide concentration, reduced to the weight of elemental sulfur, at 1.0 to 1.7% by weight based on the weight of naphthalene.

12. A process of claim 11 wherein the catalytic substance mixture includes an oxide of a metal selected from the group consisting of tungsten, titanium, zirconium, tantalum, cesium, molybdenum, chromium, niobium, nickel, aluminum, iron and silver.

13. A process of claim 11 wherein the catalytic substance mixture includes iron sulfate.

* * * * *